United States Patent [19]
Snaper et al.

[11] Patent Number: 5,431,694
[45] Date of Patent: Jul. 11, 1995

[54] BIO-OPERABLE POWER SOURCE

[76] Inventors: Alvin A. Snaper, 2800 Cameo Cir., Las Vegas, Nev. 89107; Bernard R. Gelbaum, 127 Ruskin Rd., Buffalo, N.Y. 14226; Daniel Gelbaum, 48 Bellevue, San Rafael, Calif. 94901

[21] Appl. No.: 218,150

[22] Filed: Mar. 25, 1994

Related U.S. Application Data

[63] Continuation of Ser. No. 931,815, Aug. 18, 1992, abandoned.

[51] Int. Cl.6 .............................................. A61N 1/00
[52] U.S. Cl. ................................................... 607/35
[58] Field of Search .................... 607/35; 128/672; 604/891.1

[56] References Cited

U.S. PATENT DOCUMENTS

| | | | |
|---|---|---|---|
| 3,456,134 | 7/1969 | Ko | 607/35 |
| 3,659,615 | 5/1972 | Enger | 128/419 B |
| 3,943,936 | 3/1976 | Rasor et al. | 128/419 P |
| 4,185,621 | 1/1980 | Morrow | 128/672 |
| 4,481,950 | 11/1984 | Duggan | 607/9 |
| 4,690,143 | 9/1987 | Schroeppel | 128/419 B |
| 4,735,195 | 4/1988 | Blum et al. | 128/25 R |
| 4,989,611 | 2/1991 | Zanetti et al. | 128/695 |

FOREIGN PATENT DOCUMENTS

| | | | |
|---|---|---|---|
| 0026364 | 2/1978 | Germany | 607/35 |
| 2729223 | 1/1979 | Germany | 607/35 |
| 4032812 | 11/1991 | Japan | 607/35 |
| 1220677 | 1/1971 | United Kingdom | 607/35 |

OTHER PUBLICATIONS

Gerliczy et al "Solef PVDF Biaxially Oriented Piezo- and Pyro- Electric Films for Transducers" Sensors and Actuators 12 (1987) 207-233 pp. 219, 220.
Parsonnet et al., "Pacemaker using Biologic Energy Sources," 1963, pp. 174-177.
Meyers et al., "Biologically Energized Cardiac Pacemaker", Apr. 1963, p. 83.
"Ferroelectric Polymers and Their Applications" Marcus, Aug. 1981.

*Primary Examiner*—William E. Kamm
*Assistant Examiner*—Marianne Parker
*Attorney, Agent, or Firm*—Donald D. Mon

[57] ABSTRACT

A bio-operated implant system for implantation inside a human body. A piezoelectric generator in the form of a flexible sheet of poled polyvinylidene fluoride structurally that is attached in surface-to-surface contiguity with a skeletal number, which flexes with negligible elongation of its surface, is connected in circuit with a power consuming device such as a pacemaker, to a rectifier, and to a power storage device such as a condenser or battery. The generator generates in alternating voltage, which is rectified to direct current, which is supplied to the power consuming device on demand.

4 Claims, 1 Drawing Sheet

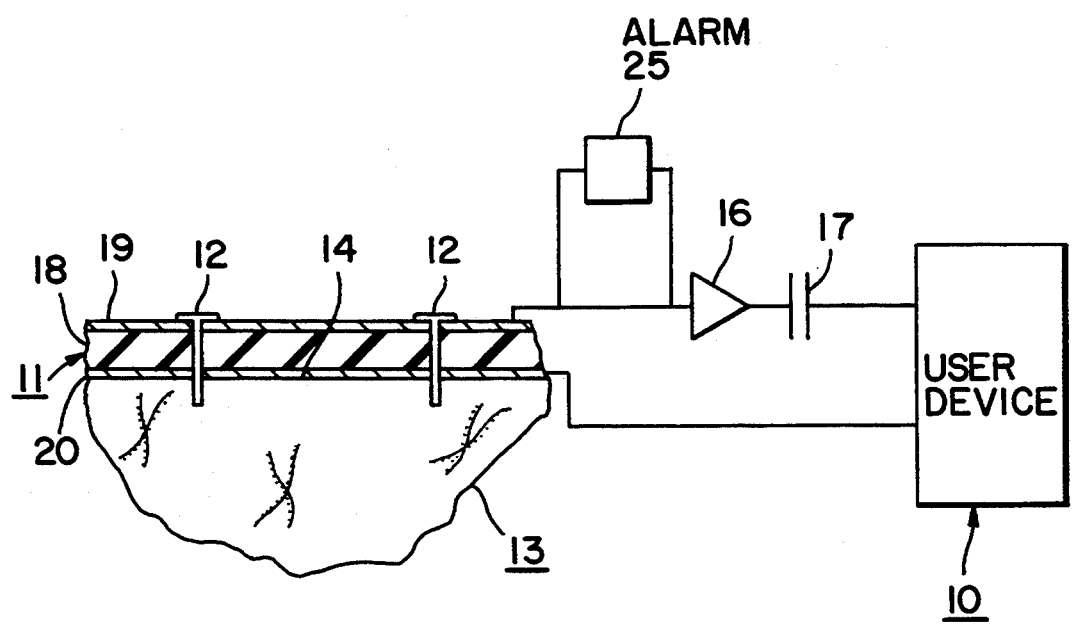

BIO-OPERABLE POWER SOURCE

This is a continuation of application Ser. No. 07/931,815 filed on Aug. 18, 1992, now abandoned.

FIELD OF THE INVENTION

A power source whose energy is derived from changes in shape responsive to autonomic movements of the human body.

BACKGROUND OF THE INVENTION

Batteries are widely used to provide power to operate devices which are portable and are thereby not amenable to connection with fixed generators or outlets. Sometimes the batteries are carried as a separate pack and can be recharged or replaced. These enjoy a substantial employment, but only when they can readily be connected to the devices which they are to power.

There are, however, many installed devices to which access is not only restricted, but which is risky. In such installations the battery must be very closely coupled physically to the device which it powers. In medical devices that are implanted, for example, the battery which powers a device such as a pacemaker must be implanted along with the pacemaker or be connected to it by leads which pass through the body. The latter involves many problems, not the least of which is infection, but the battery is rechargable or replaceable.

However, if the battery is implanted, it must someday be replaced, and its limited life is the major failure mechanism in conventional pacemaker designs. Replacement of batteries is a surgical procedure with inherent risks of its own.

Numerous suggestions have been made for recharging an implanted energy source, but all of them which are known to the instant inventors involve exposing the wearer to attendant risks.

While devices implanted in the body represent the presently best-known application of this invention, the power source of this invention is also useful wherever there is a movable element that can exert a bending force on a tape-like current generator.

It is an object of this invention to provide a power source that provides an electrical charge to a storage device as the consequence of a bending autonomic force. An example is an implanted capacitor or battery, coupled to the source, the storage device being connectible to a user device such as a pacemaker. The source itself is mounted to structure which exerts a bending action on it, such as muscle tissue, lung tissue, or a rib.

BRIEF DESCRIPTION OF THE INVENTION

A power source according to this invention includes a charge storage device and a plate-like flexible piezoelectric generator which while being bent generates an electrical current to charge the storage device. The storage device is adapted to be connected to a user device such as a pacemaker. The generator is inherently adaptable to be attached to structure which can repetitively bend it, and while it is being bent, to generate an electrical current. It inherently operates as an ac generator, but rectifier means rectifies its output to dc.

The bending action is conveniently provided by heart muscle, lung expansion, or bending of a rib, as examples. Examples of user devices are pacemakers and insulin pumps. The applications of this invention are not limited to such devices, or even to implants, but may be used with any user device which is located near to a flexural member.

The above and other features of this invention will be fully understood from the following detailed description and the accompanying drawing, in which:

BRIEF DESCRIPTION OF THE DRAWING

FIG. 1 is a schematic view, partly in cutaway cross-section, showing a power source according to this invention.

DETAILED DESCRIPTION OF THE INVENTION

FIG. 1 shows a user device 10 such as a pacemaker, which is to be powered by an electrical current derived from a generator 11. The generator is a flexible plate-like piezoelectric body attached by means such as staples 12 to an anatomical element 13, which under goes autonomic flexural movement.

Examples of element 13 are heart muscle, lung tissue and ribs, all of which in their normal function flex to provide a bending movement at their surface 14. Staples 12 are given as merely one example of means to attach the piezoelectric body to the element 13. Sutures and adhesives are other useful means to attach the generator to the anatomical element. What is important is that the element flexes, and when it does, it bends the generator.

Conventional rectifiers and storage means are utilized to couple generator 11 to user device 10. A simple rectifier 16 and capacitor 17 are shown as means to convert the alternating voltages from generator 11 to dc to be applied to user device 10.

The body of generator 11 is a piezoelectric film comprising a polyvinylidine fluoride ("PVDF"), semicrystalline resin processed to align its molecules ("poling"). This material is available from Atochem North America, Piezo Film Sensor Division, Valley Forge, Pa. 19482 under its mark Kynar. It includes a layer 18 of PVDF sandwiched between two metal layers 19, 20 which form terminals for the generator.

The PVDF is preferably bi-axially stretched at just below the polymer's softening point with subsequent annealing and stretching to change its crystalline structure to the beta phase. Therefore, the film is processed by "poling", of which the two principal methods are thermal and corona. Both are well-known. These specifics of the manufacturers processes are unimportant to this invention.

The capacitor shown in the drawing is quite suitable for a storage device in this system. In fact, because it does not involve chemical reactivity, it is superior to batteries, although batteries are another suitable form of storage device. Capacitors may be embedded as stacked layers, in forms well-known in the art. The selection of rectifier and capacitor, and of other circuit elements which might be useful is well within the skill of any good electronic designer.

The details of the user device are unimportant to this invention. User devices such as pacemakers require a prescribed voltage and current capacity both of which can be supplied by the described generator, and which can be provided with circuit means to attend to excessive charge or voltage. Capacitors adequate to operate the user device for long periods of time can readily be provided.

Incidentally, because this invention is intended to operate as the consequence of repetitive autonomic movement, it can also serve as an alarm in the event that such movement ceases. An alarm 25 is schematically shown in the circuit from generators 11, which will alert the user should generation of a charge cease.

This invention is not to be limited by the embodiment shown in the drawings and described in the description, which is given by way of example and not of limitation, but only in accordance with the scope of the appended claims.

I claim:

1. A bio-operated implant system adapted for implantation inside a human body, said human body including a skeletal member which repetitively flexes with negligible elongation of its surface, said system comprising:

a power-consuming means for responding to a physiological requirement of said human body; and a source of electrical voltage and current comprising a flexible sheet of polyvinylidene fluoride, poled to align its molecules thereby to form a piezoelectric generator, said sheet having a face sufficiently flexible to conform to said surface of said skeletal member, means for structurally attaching said sheet in surface-to-surface contiguity with said surface of said skeletal member so as to undergo negligible stretching when said surface flexes, said sheet generating an alternating voltage and current when flexed by the flexure of the skeletal member, rectifier means connected in circuit with said sheet for rectifying said alternating current, power storage means for storing energy from said rectifier means connected in circuit to said rectifier means and to said power-consuming means, said sheet also being connected in circuit with said power consuming means;

whereby alternating voltage and current are developed by said sheet by its being flexed with negligible extension, and its output is directed through said rectifier means to be rectified and then to said power storage means to be stored, said power storage means thereby providing power to the power-consuming means.

2. A system according to claim 1 in which said power-consuming means is a pacemaker or an insulin pump.

3. A system according to claim 1 in which said power storage means is a capacitor.

4. A system according to claim 1 in which alarm means is connected to said power storage means to indicate insufficiency of available power.

* * * * *